US012606362B2

(12) United States Patent
Das et al.

(10) Patent No.: US 12,606,362 B2
(45) Date of Patent: Apr. 21, 2026

(54) CONTROL MECHANISM FOR A DISPENSING DEVICE

(71) Applicant: Reckitt & Colman (Overseas) Hygiene Home Limited, Slough (GB)

(72) Inventors: Avijit Das, Hull (GB); Cliff Li, Shenzhen City (CN); Walter Sordo, Trento (IT); Umberto Toniolo, Hull (GB); Christopher Witty, Hull (GB); Charles Yao, Shenzhen City (CN)

( * ) Notice: Subject to any disclaimer, the term of this patent is extended or adjusted under 35 U.S.C. 154(b) by 662 days.

(21) Appl. No.: 17/642,459

(22) PCT Filed: Sep. 25, 2020

(86) PCT No.: PCT/EP2020/076941
§ 371 (c)(1),
(2) Date: Mar. 11, 2022

(87) PCT Pub. No.: WO2021/063836
PCT Pub. Date: Apr. 8, 2021

(65) Prior Publication Data
US 2022/0306373 A1    Sep. 29, 2022

(30) Foreign Application Priority Data
Oct. 1, 2019    (GB) ...................................... 1914114

(51) Int. Cl.
B05B 12/02      (2006.01)
A61L 9/14       (2006.01)
B65D 83/26      (2006.01)

(52) U.S. Cl.
CPC .............. B65D 83/262 (2013.01); A61L 9/14 (2013.01); A61L 2209/11 (2013.01)

(58) Field of Classification Search
CPC ....... B65D 83/262; A61L 9/14; A61L 2209/11
(Continued)

(56) References Cited

U.S. PATENT DOCUMENTS 5,062,611 A * 11/1991 Hatton .................. F16K 31/041
                                                          251/284
2012/0223625 A1* 9/2012 Klemm .................. H02K 11/30
                                                          310/83
(Continued)

FOREIGN PATENT DOCUMENTS

CN          2902293 Y      5/2007
CN          202822219 U    3/2013

OTHER PUBLICATIONS

International Search Report and Written Opinion of the International Searching Authority for corresponding application PCT/EP2020/076941 dated Feb. 1, 2021.
(Continued)

*Primary Examiner* — Gabriel Agared
(74) *Attorney, Agent, or Firm* — Norris McLaughlin, PA

(57) ABSTRACT

The present invention relates to a control mechanism (10) for a dispensing device (50). The control mechanism (10) includes a motor (12), a gear arrangement (14) operably connected to the motor (12); and an actuator (15) operably connected to the gear arrangement (14). In use, the actuator (15), under the operation of the motor (12), is configured to actuate an outlet (38) of a container (40) to dispense fluid from within the container (40). The gear arrangement (14) is configured such that a low torque motor (12) may be used to dispense the fluid.

13 Claims, 4 Drawing Sheets

(58) Field of Classification Search
USPC .......................................................... 318/15
See application file for complete search history.

(56) References Cited

U.S. PATENT DOCUMENTS

| | | | | |
|---|---|---|---|---|
| 2014/0276384 A1* | 9/2014 | Schwab | .................. | A61M 5/20 |
| | | | | 604/82 |
| 2015/0328405 A1* | 11/2015 | Metzner | .............. | A61M 5/2046 |
| | | | | 604/154 |
| 2016/0215862 A1* | 7/2016 | Telep | ........................ | F16H 1/28 |
| 2016/0298749 A1* | 10/2016 | Burger | .................... | H02P 27/06 |
| 2017/0234308 A1* | 8/2017 | Buckley | .................. | F04B 53/22 |
| | | | | 417/53 |
| 2018/0368360 A1* | 12/2018 | Vasconcelos | .......... | A01K 11/00 |
| 2020/0207239 A1* | 7/2020 | Navatte | .................. | F16H 55/26 |

OTHER PUBLICATIONS

Combined Search and Examination Report for corresponding application GB 1914114.2 dated Mar. 4, 2020.

* cited by examiner

CONTROL MECHANISM FOR A DISPENSING DEVICE

This is an application filed under 35 USC 371 based on PCT/EP2020/076941, filed 25 Sep. 2020, which claimed priority to GB 1914114.2 filed 1 Oct. 2019. The present application claims the full priority benefit of all prior applications and incorporates by reference their full disclosures as if set forth herein.

TECHNICAL FIELD OF THE INVENTION

The present invention relates to a control mechanism for a dispensing device, and specifically to a control mechanism for controlling the dispensing of fluid from a container (e.g. a pressurised aerosol container).

BACKGROUND TO THE INVENTION

It is known to provide automatic dispensing devices (e.g. air fresheners) which dispense a fluid, for example in the form of an aerosol, under the operation of a control mechanism. The control mechanism may act periodically to dispense the fluid at set time intervals. Additionally or alternatively, the control mechanism may act under a user input, e.g. a push button or the like.

Conventionally, the control mechanism may take the form of a motor and gear arrangement which, under the operation of the motor, may cause corresponding movement of an actuator. The movement of the actuator may act to cause dispensing of fluid from a container, for example, via acting on a push valve on the container. Known arrangements may include a DC motor having a driving voltage of approximately 3V, powered by a pair of 1.5V AA batteries. Such an arrangement may be necessary to provide sufficient torque to enable rotation of the gear arrangement to move the actuator with sufficient force to actuate dispensing of the fluid from the container.

It would be advantageous to provide a control mechanism with a reduced power and/or torque requirement from a packaging, weight and cost point of view.

It is therefore an aim of an embodiment or embodiments of the invention to overcome or at least partially mitigate one or more problems associated with the prior art.

SUMMARY OF THE INVENTION

According to an aspect of the invention there is provided a control mechanism for controlling dispensing of fluid from a container, the control mechanism comprising: a motor; a gear arrangement operably connected to the motor; and an actuator operably connected to the gear arrangement and configured to actuate an outlet of the container to dispense fluid therefrom under operation of the motor; wherein the gear ratio of the gear arrangement is at least 190:1.

Advantageously, providing a gear mechanism having a gear ratio of at least 190:1 allows for a motor with a lower torque output to be used to drive the gear arrangement. Such a motor may be smaller, less costly and have a lower power/voltage requirement when compared with motors having a higher torque output (as may be required for gear arrangements having a lower gear ratio).

In embodiments, the gear ratio of the gear arrangement is at least 200:1, or at least 220:1 or at least 240:1 or at least 260:1. The gear ratio of the gear arrangement may be no more than 340:1, or no more than 320:1, or no more than 300:1, or no more than 280:1, or no more than 260:1, for example. In presently preferred embodiments the gear ratio of the gear arrangement is approximately 279:1.

In embodiments the gear arrangement comprises a driver gear (pinion) operably connected to the motor. The driver gear is configured to rotate under the operation of the motor. Further, the gear arrangement may comprise a driven gear. The driven gear may be configured to rotate upon rotation of the driver gear. For example, in some embodiments the driver gear and the driven gear are directly coupled to one another to rotate the driven gear upon rotation of the driver gear/motor. In other embodiments, the gear arrangement may comprise one or more intermediary gears operably coupled to the driver gear, driven gear and/or one or more further intermediary gears.

In some embodiments the one or more intermediary gears may comprise two or more sets of teeth. For example, in some embodiments the one or more intermediary gears may comprise a compound gear having a primary set of teeth and a secondary set of teeth. The primary and secondary sets of teeth may be concentric and rotate about the same axis. In some embodiments the secondary set of teeth may comprise a greater number of teeth than the primary set of teeth. In presently preferred embodiments, the primary set of teeth may comprise a greater number of teeth than the secondary set of teeth. The diameter of the primary set of teeth may be greater than the diameter of the secondary set of teeth. The primary set of teeth may be operably coupled to a preceding gear in the gear arrangement. The secondary set of teeth may be operably coupled to a subsequent gear in the gear arrangement.

Advantageously, using concentric compound gears may achieve a higher gear ratio of the gear arrangement without substantially increasing the overall size of the gear arrangement.

In embodiments the gear arrangement comprises a driver gear (pinion), a first intermediary gear, a second intermediary gear and a driven gear. In embodiments wherein the first and second intermediary gears comprise concentric gears, the driver gear (pinion) may be operably coupled to the primary set of teeth on the first intermediary gear, the secondary set of teeth on the first intermediary gear may be coupled to the primary set of teeth on the second intermediary gear and the secondary set of teeth on the second intermediary gear may be operably coupled to the driven gear.

The driver gear (pinion) may comprise from 5 to 25 teeth, such as 6 to 20, or advantageously from 7 to 15. In a particular embodiments the driver gear (pinion) comprises 9 teeth.

The one or more intermediary gears may comprise a primary set of teeth having at least 40 teeth, or at least 50 teeth, or at least 60 teeth, or at least 70 teeth, for example. The one or more intermediary gears may comprise a primary set of teeth having no more than 100 teeth, or no more than 90 teeth, or no more than 80 teeth, or no more than 70 teeth, or no more than 60 teeth, for example. In some embodiments the gear arrangement comprises a first intermediary gear having a primary set of teeth having 56 teeth, and a second intermediary gear having a primary set of teeth having 67 teeth.

The one or more intermediary gears may comprise a secondary set of teeth having no more than 25 teeth, or no more than 20 teeth, or no more than 15 teeth, or no more than 10 teeth, or no more than 5 teeth, for example. The one or more intermediary gears may comprise a secondary set of teeth having at least 5 teeth, or at least 10 teeth, or at least 15 teeth, for example. In presently preferred embodiments, the one or more intermediary gears comprise a secondary set of teeth having 10 teeth.

The driven gear may comprise at least 40 teeth, or at least 50 teeth, or at least 60 teeth, or at least 70 teeth, for example. The driven gear may comprise no more than 100 teeth, or no more than 90 teeth, or no more than 80 teeth, or no more than 70 teeth, or no more than 60 teeth, for example. In some embodiments the driven gear comprises 67 teeth.

In embodiments the actuator may be integrally formed or otherwise connected to a gear of the gear arrangement and be configured to actuate an outlet of the container to dispense fluid therefrom under operation of the motor. For example, in some embodiments the actuator is integrally formed or otherwise connected to the driven gear of the gear arrangement. In embodiments, the actuator may comprise a portion of the driven gear of the gear arrangement.

In use, the actuator may be moveable between a first position and a second position under the operation of the motor. The first position may be referred to herein as a resting position—i.e. a position in which the actuator, in use, is not acting on an outlet of an associated container. The second position may be referred to herein as an actuating position—i.e. a position wherein the actuator is acting or, in moving to the second position from the first position, has acted on the outlet of the associated container.

In its first position, the actuator may be positioned such that it applies little or no force on the outlet of the container. For example, in its first position the actuator may be positioned away from/out of contact with the outlet of the container. Alternatively, in its first position, the actuator may be positioned in contact with the outlet of the container but positioned such that any force applied to the outlet due to the contact is less than the force required to actuate the outlet to dispense fluid from the container.

As discussed herein, in moving to its second position the actuator may actuate the outlet to dispense fluid therefrom. In embodiments, in moving to its second position, the actuator may be configured to act against a surface of the outlet, for example, to displace the outlet. In embodiments, the actuator may be configured, in use, to act against an upper surface of the outlet to displace the outlet in a substantially downwards direction. Displacement of the outlet may cause a valve associated with the outlet to open thereby allowing fluid within the container to be dispensed therefrom.

In embodiments, the actuator may be biased to the first position. In such embodiments, the motor and gear arrangement must work against said bias in order to move the actuator into its second position thereby actuating dispending of fluid from the container. Providing the bias allows for the control mechanism to be automatically reset after actuation of the outlet of the container—i.e. by moving the actuator back to the first position.

In embodiments, the bias may be provided by the outlet of the container. For example, the outlet may comprise a push button valve which may be acted on by the actuator, in use, to dispense the fluid, e.g. by pushing against a bias provided by the valve to move the valve from a closed to an open position. In such embodiments, the motor may be configured such that, in use, it may be de-energised during (e.g. relying on gear inertia to complete the spray) or after actuation of the outlet of the container allowing the bias provided by the valve to move the actuator back to its first position.

In alternative embodiments, the control mechanism may comprise a biasing member configured to bias the actuator to its first position. For example, the control mechanism may comprise a spring or a resilient member suitably positioned within the control mechanism to provide a biasing force acting against the movement of the actuator from the first position to the second position. Alternatively or additionally, the actuator may comprise elastomeric/resilient material to aid rebound/bias of the actuator.

In embodiments where the gear ratio of the gear arrangement is above a certain level, any bias provided, for example by the outlet of the container, may not be sufficient to effectively reset the control mechanism after use. Accordingly, in some embodiments the motor may be configured to be able to be run in reverse to thereby rotate the gear arrangement in the opposite sense and move the actuator back to its first position following actuation of the outlet of the container.

The motor may comprise a driving voltage range of approximately 1 to 3.0 V.

In presently preferred embodiments the driving voltage of the motor may be approximately 1.5V. Advantageously, using a motor with a driving voltage of approximately 1.5V allows for the use of a single, 1.5V AA battery to be used to power the control mechanism. In this way, improvements in terms of packaging space and potentially cost can be realised when compared with two battery systems (e.g. 3.0 V systems).

In embodiments the motor may comprise a stall torque of no more than 70 g·cm, or no more than 60 g·cm, or no more than 50 g·cm, or no more than 40 g·cm, or no more than 30 g·cm. The motor may comprise a stall torque of at least 20 g·cm, or at least 30 g·cm, or at least 40 g·cm, for example. In presently preferred embodiments the motor comprises a stall torque of approximately 35 g·cm.

To account for the lower torque output of a 1.5V motor when compared with a 3.0V motor, the gear arrangement is provided with a gear ratio of at least 190:1, which may provide sufficient output torque from the gear arrangement to move the actuator against any inherent bias in the outlet of the container and cause dispensing of fluid from the container.

In embodiments the control mechanism comprises means for controlling operation of the device. For example, the control mechanism can include one or more processors for controlling operation of the control mechanism in accordance with one or more stored instructions. The one or more instructions may relate to the timing/periodicity of the actuation of the outlet of the container.

One or more components of the control mechanism may be provided on a circuit board. The circuit board can include motor terminals for electrically coupling the motor to further components of the control mechanism. For example, the circuit board may include motor terminals configured to receive respective motor contacts of a motor for electrically coupling the motor to other components of the control mechanism. The circuit board can include power terminals for electrically coupling a source of power, e.g. one or more batteries for powering components of the control mechanism.

The one or more processors may comprise a microprocessor. The microprocessor may have a driven voltage of less than 2.0 V, such as from 1.1 to 1.6 V. Advantageously, the control mechanism may be powered using a single 1.5V AA battery and may therefore be suitable for embodiments which comprise a motor having a driven voltage of approximately 1.5V. In some embodiments the microprocessor may comprise (or be otherwise associated with) a transformer arrangement where the operating voltage of the microprocessor exceeds the output voltage of the power source for the control mechanism.

The control mechanism may include a switch arrangement, for example, for switching an operating mode of the control mechanism. Different operating modes may relate to different time intervals between consecutive actuations of the outlet of the container, or a number of consecutive actuations at a fixed interval.

In embodiments, components of the control mechanism (e.g. the power terminals, the motor terminals) may be provided integral with, mounted to or printed on the circuit board. Advantageously, configuring the control mechanism in this manner may reduce packaging space and/or the need for wiring or cables between components thereof.

According to a further aspect of the invention there is provided a dispensing device, the dispensing device comprising the control mechanism of the preceding aspect of the invention and a housing.

In embodiments, the housing comprises a first compartment for receiving a container. The first compartment may be configured such that when positioned within the first compartment, an outlet of the container is positioned proximal to the actuator of the control mechanism such that the control mechanism may be used to actuate the outlet to dispense fluid from within the container. The first compartment may be accessible such that the container may be replaced, as necessary. For example, in some embodiments the first compartment may include a moveable (e.g. hinged) or removable cover for providing access to the first compartment for replacing the container.

The housing may further define a second compartment for housing the control mechanism. The second compartment may, in embodiments be primarily inaccessible to prevent interference with the control mechanism. The second compartment may include a moveable (e.g. hinged) or removable cover for providing access to at least a portion of the second compartment for example, to interact with a switch mechanism of the control mechanism, or to replace the battery.

In embodiments, the dispensing device may be configured such that the control mechanism may be provided directly above a container, in use. In this way, the actuator of the control mechanism may act downwardly on the outlet of the container to dispense fluid therefrom. The control mechanism may contribute to a significant portion of the overall weight of the dispensing device, particularly where the amount of fluid in the container is low, which may potentially result in the dispensing device becoming top heavy and unstable. However, this may be addressed through the improvements in packaging and weight realised by the control mechanism of the present invention which may be sufficient to reduce or eliminate any instability caused by having a control mechanism positioned above the container within the dispensing device.

DETAILED DESCRIPTION OF THE INVENTION

In order that the invention may be more clearly understood one or more embodiments thereof will now be described, by way of example only, with reference to the accompanying drawings, of which:

6

Figure 4:
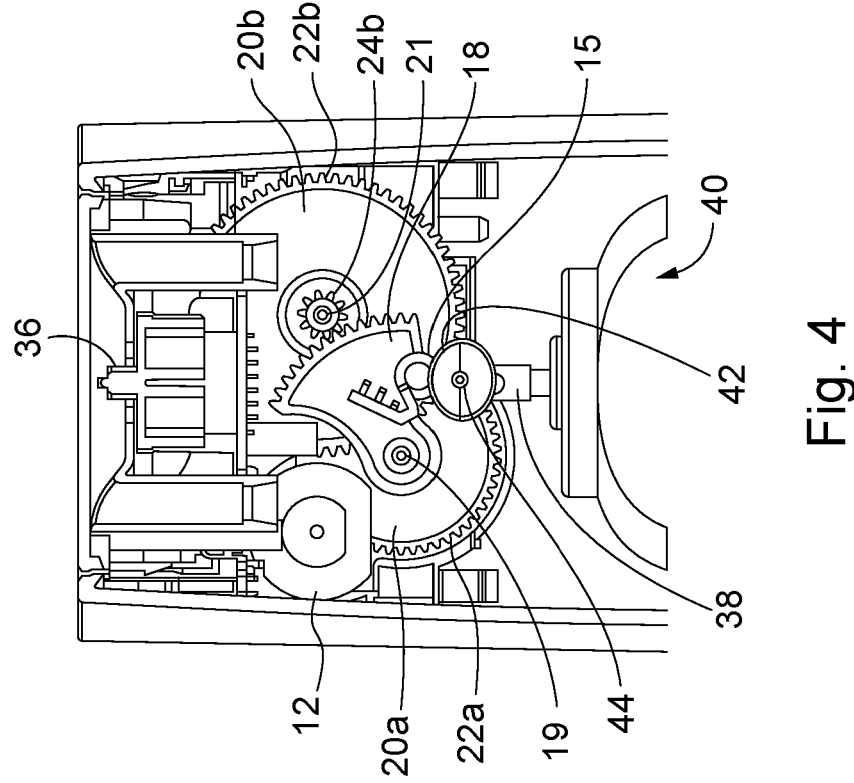
Figure 3:
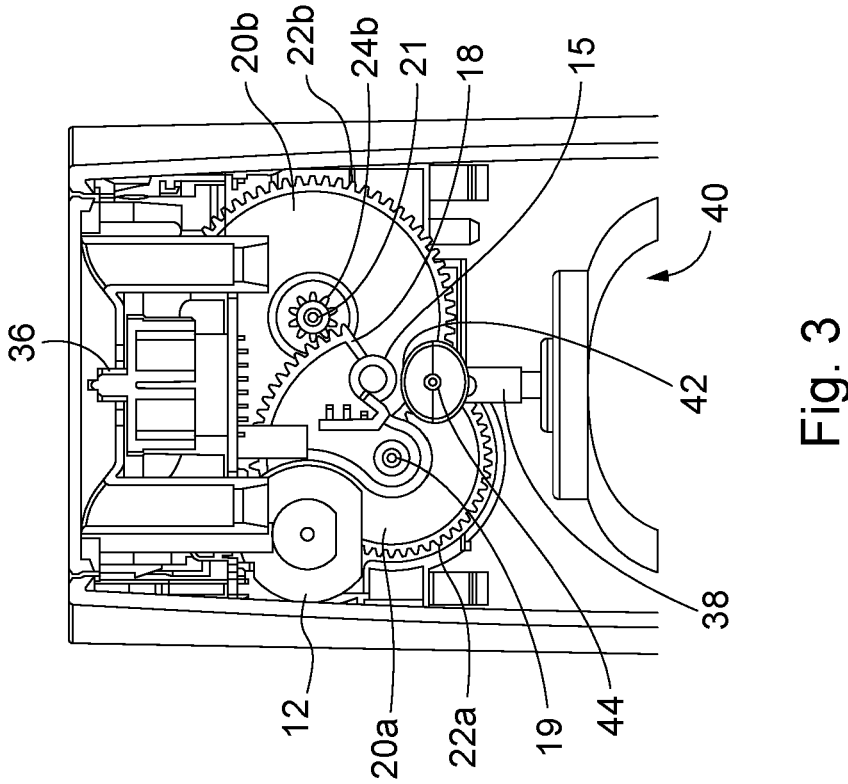
Figure 5:
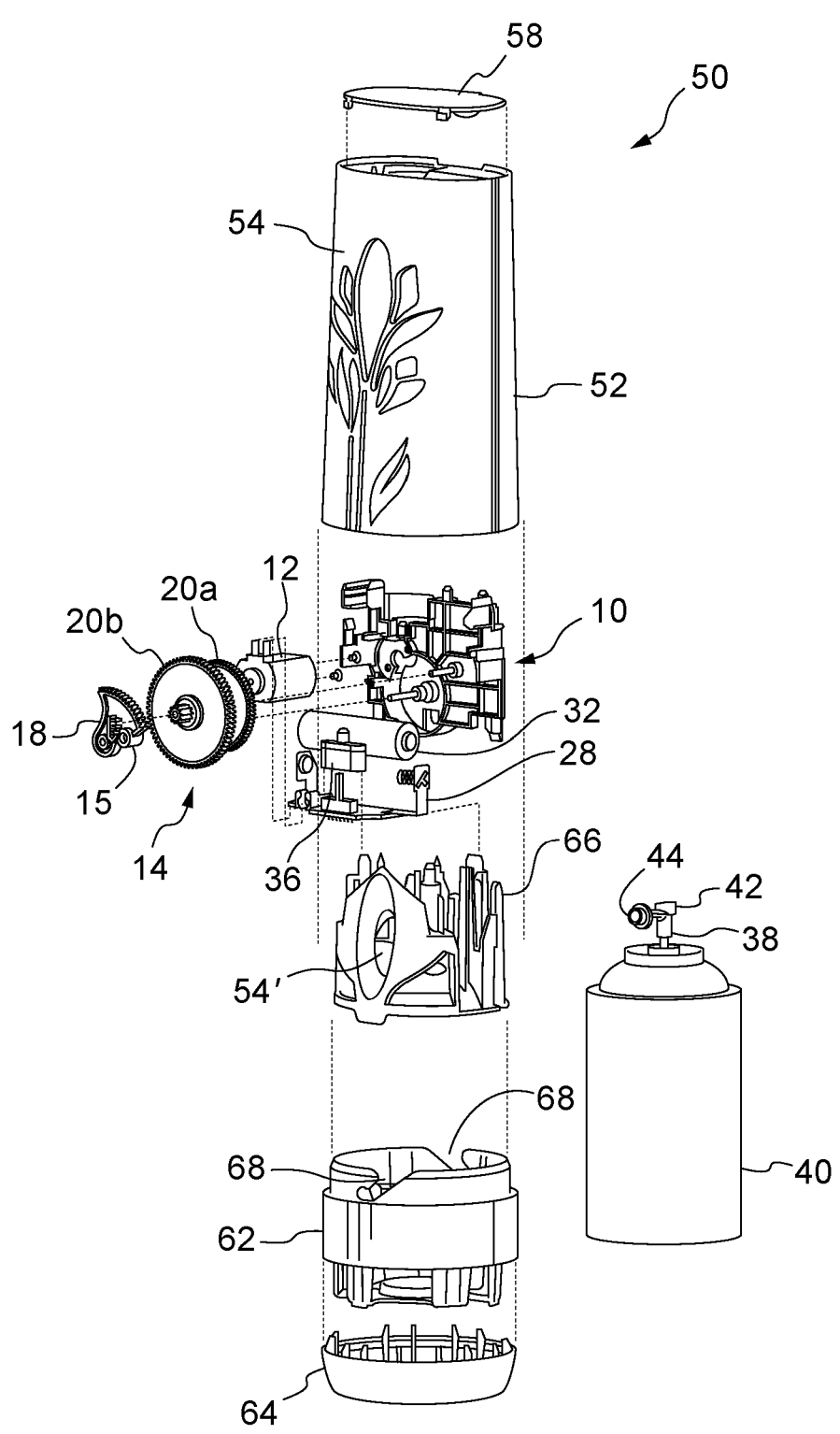
Figure 6:
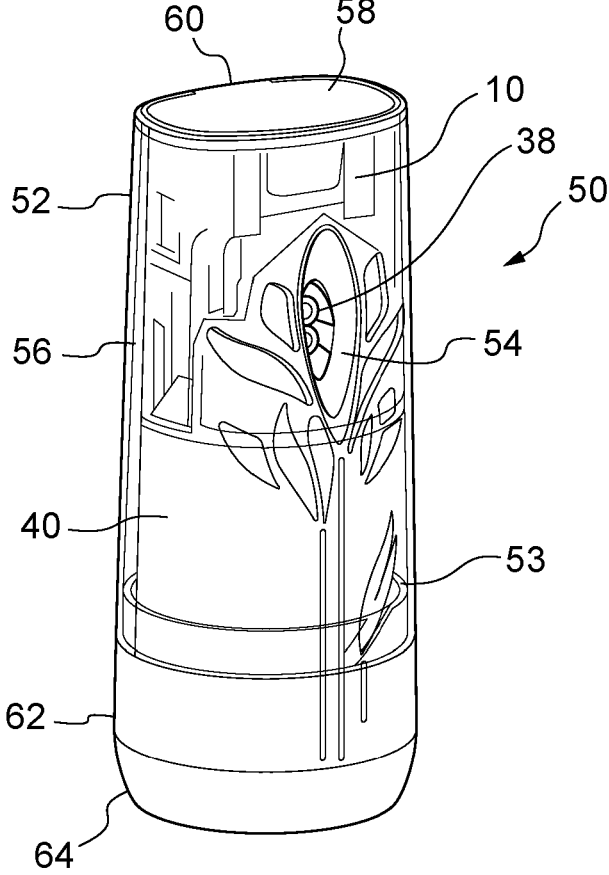

FIG. 3 is a perspective view of a section of the control mechanism shown in the preceding Figures;

FIG. 4 is a perspective view of an embodiment of a dispensing device in accordance with the invention;

FIG. 5 is an exploded view of the housing and the control mechanism in accordance with the invention;

FIG. 6 is a perspective view of the housing comprising the control mechanism in accordance with the invention.

An embodiment of a control mechanism 10 in accordance with the invention is shown in the Figures.

The control mechanism 10 comprises a motor 12, a gear arrangement 14 operably connected to the motor 12; and an actuator 15 operably connected to the gear arrangement 14. In use, the actuator 15 is configured to actuate an outlet 38 of a container 40 to dispense fluid from within the container 40. The actuator 15 is caused to actuate the outlet 38 under the operation of the motor 12 as is described herein.

The gear arrangement 14 includes a driver gear (pinion) 16, a driven gear 18, and first and second intermediary gears 20a, 20b which comprise gears having a primary set of teeth 22a, 22b and a secondary set of teeth 24a, 24b, respectively. The pinion 16 is rotatable about first axis, the first intermediary gear 20a and the driven gear 18 are independently rotatable about a second axis, and the second intermediary gear 20b is rotatable about a third axis. The first axis is defined by a motor shaft 17 for providing a rotational output from the motor 12. The second and third axes are defined, respectively, by first and second axles 19, 21. In the illustrated embodiment, the first and second axles 19, 21 are fixed shafts about which the corresponding gears 18, 20a, 20b are rotatable. In another embodiment, the compound gears may be formed integrally with shafts, and the axles created by corresponding holes that receive the shafts The pinion 16 is operably connected to the motor 12 via the motor shaft 17. In turn, the pinion 16 is operably coupled to the primary set of teeth 22a on the first intermediary gear 20a, the secondary set of teeth 24a on the first intermediary gear 20a are operably coupled to the primary set of teeth 22b on the second intermediary gear 20b and the secondary set of teeth 24b on the second intermediary gear 20b are operably coupled to the driven gear 18. In this way, rotation of the pinion 16 under operation of the motor 12 causes corresponding rotation of the first intermediary gear 20a, second intermediary gear 20b and driven gear 18 about their respective axles 19, 21 to cause movement of the actuator 15 between a first and second position, as discussed herein.

This arrangement allows for the provision of a relatively high gear ratio when compared with conventional control mechanisms of this type. Specifically, in the illustrated embodiment, the pinion 16 comprises 9 teeth, the first intermediary gear 20a comprises 56 teeth in its primary set of teeth 22a and 10 teeth in its secondary set of teeth 24a, the second intermediary gear 20b comprises 67 teeth in its primary set of teeth 22b and 10 teeth in its secondary set of teeth 24b, and the driven gear 18 comprises 67 teeth. Configuring the gear arrangement 14 in this way provides a gear ratio of approximately 279:1 which allows for a relatively low torque motor 12 to be used in the control mechanism 10. Providing this gear ratio allows for use of a motor 12 having a driving voltage of approximately 1.5V. This in turn allows for the control mechanism 10 as a whole to be powered by a single 1.5V AA battery 32. This is in contrast to conventional control mechanisms which, due to the required torque output of the motor, may use motors with higher rated voltages powered by a larger voltage battery/battery arrangement (e.g. 2 or more AA batteries), thereby providing benefits in terms of cost, weight and packaging.

It will be appreciated that other configurations of the gear arrangement 14 may be provided which result in a suitably high gear ratio, and the invention is not limited in this sense. For example, the pinion 16 may comprise no more than 5 teeth, or no more than 10 teeth, or no more than 15 teeth. Each of the intermediary gears 20*a*, 20*b* can comprise a primary set of teeth 22*a*, 22*b* having at least 40 teeth, or at least 50 teeth, or at least 60 teeth, or at least 70 teeth, for example. Further, each of the intermediary gears 20*a*, 20*b* can comprise a secondary set of teeth 24*a*, 24*b* having no more than 5 teeth, or no more than 10 teeth, or no more than 15 teeth. The driven gear 18 can comprise at least 40 teeth, or at least 50 teeth, or at least 60 teeth, or at least 70 teeth. The choice of configuration of the gears 16, 18, 20*a*, 20*b* may be selected based on the required gear ratio of the control mechanism 10 to provide sufficient output torque to actuate dispensing of the fluid from the container 40. For example, gears 16, 18, 20*a*, 20*b* may be configured to provide a gear ratio of at least 200:1, or at least 220:1, or at least 240:1, or at least 260:1, for example.

The actuator 15 is integrally formed with the gear arrangement 14. Specifically, the actuator 15 is integrally formed with the driven gear 18 such that upon rotation of the driven gear 18 about the first axle 19, the actuator 15 is caused to be moved between a first (resting) position—see FIG. 3—and a second (actuating) position—see FIGS. 1 and 2. The operational use of the control mechanism 10 to control movement of the actuator 15 between the first and second positions is described in detail, below.

The control mechanism 10 includes a control system including a processor (not shown) provided on a circuit board 28. The processor is configured to control operation of the control mechanism 10 in accordance with one or more stored instructions—e.g. instructions relating to the timing/periodicity of the actuation of the outlet 38 of the container 40. The processor comprises a microprocessor and has an operating voltage of from 0.5 to 6.0 V and a driven voltage of 1.1 to 1.6 V.

As shown, the circuit board 28 includes motor terminals 34*a*, 34*b* for receiving respective motor contacts 33*a*, 33*b* of the motor 12 for electrically coupling the motor 12 to the circuit board 28, and power terminals 30*a*, 30*b* for electrically coupling a source of power in the form of the single AA battery 32 to the circuit board 28 for powering the control mechanism 10. In the illustrated embodiment, the power terminals 30*a*, 30*b* and the motor terminals 34*a*, 34*b* are provided integral with the circuit board 28. Advantageously, configuring the control mechanism 10 in this manner may reduce packaging space and/or the need for wiring or cables between components thereof.

The illustrated control mechanism 10 additionally includes a switch arrangement 36 for controlling an operating mode of the control mechanism 10. For example, the switch arrangement 36 can be used to switch between operating modes that relate to different time intervals between consecutive actuations of an outlet of an associated container.

Figure 1:
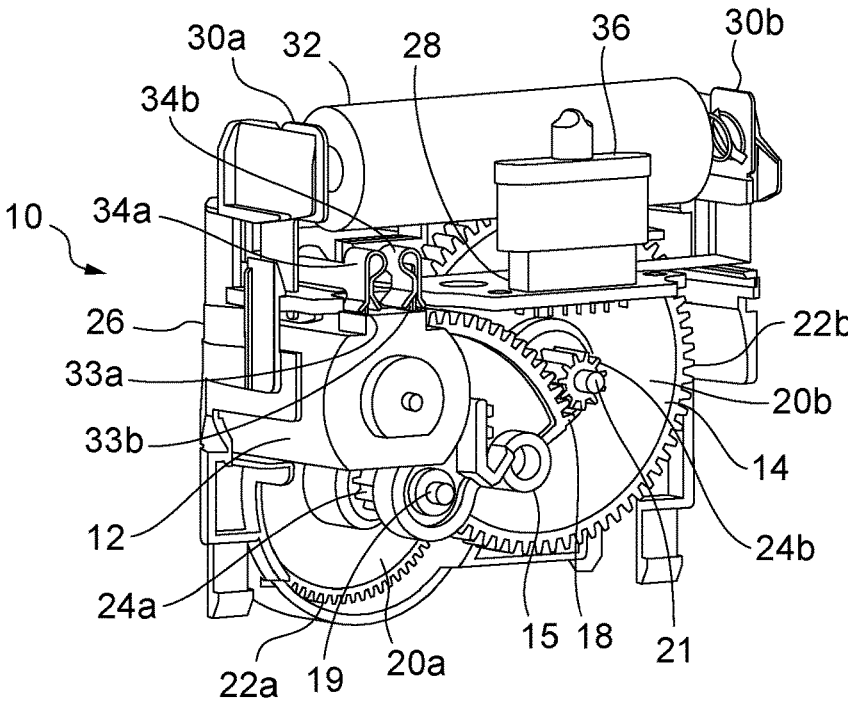
FIG. 1 is a perspective view of an embodiment of a control mechanism in accordance with the invention.
Figure 2:
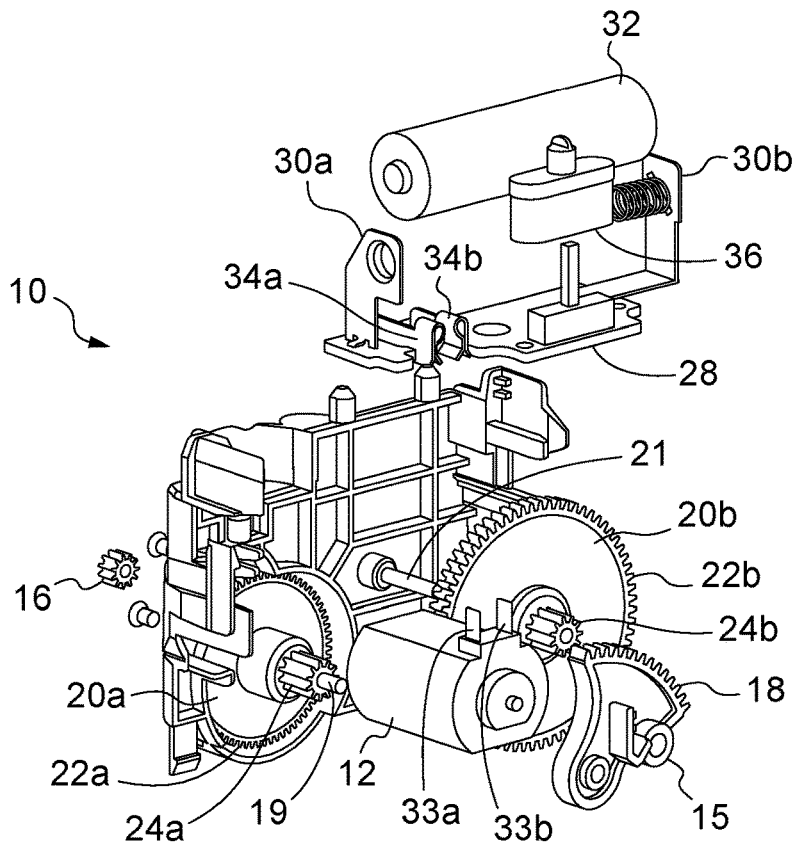
FIG. 2 is a side view of the control mechanism shown in FIG. 1.

The operational use of the control mechanism 10 is now described with reference to FIGS. 1 to 3.

In its first position, the actuator 15 is positioned in an abutting relation with an upper surface 42 of the outlet 38 of the container 40. In this position, the force provided by the contact between the actuator 15 and the upper surface 42 of the outlet 38 is less than the force required to actuate the outlet 38 to dispense fluid from the container 40. Accordingly, the first position may be referred to as a "resting" position.

The motor 12 is configured to turn in a first direction which causes a corresponding rotation of the pinion 16 as a result of the coupling of the pinion 16 to the motor 12 via the motor shaft. The coupling of the various gears of the gear arrangement 14 (as discussed above) is such that the rotation of the pinion 16 under the operation of the motor 12 causes corresponding rotation of the driven gear 18 about the first axle 19 in a clockwise direction (from the point of view shown in the Figures). This in turn causes the actuator 15 to move substantially downwards (in the orientation shown in the Figures) to its second position.

In moving to its second position, the actuator 15 is configured to actuate the outlet 38 of the container 40 to dispense fluid therefrom. Specifically, in moving to its second position, the actuator 15 pushes against the upper surface 42 of the outlet 38 to displace the outlet—e.g. downwards in the orientation shown in the Figures. This displacement may cause a valve, for example, associated with the outlet to open thereby allowing fluid within the container 40 to be dispensed therefrom.

To return the actuator 15 to its first position following actuation of the outlet 38, the motor 12 is configured to run in reverse. That is, the motor 12 is configured to turn in the opposite direction when compared with when the motor 12 is used to cause movement of the actuator 15 from the first position to the second position. In doing so, the motor is configured to cause each of the gears of the gear arrangement 14 to rotate in an opposite sense—again, when compared with their respective directions of rotation when moving the actuator from the first position to the second position—thereby causing the driven gear 18 to rotate about the first axle 19 in an anti-clockwise direction (from the point of view shown in the Figures). This in turn causes the actuator 15 to move substantially upwards (again in the orientation shown in the Figures) to its first position.

In use, the motor 12 and gear arrangement 14 may work against a bias provided by the outlet 38 of the container 40 in order to move the actuator 15 into its second position thereby actuating dispending of fluid from the container 40. This bias may, in some cases, be used to reset the control mechanism 10 after use—i.e. used to move the actuator 15 back to the first position. Additionally or alternatively, the control mechanism 10 can include a biasing member configured to bias the actuator 15 to its first position.

Where the gear ratio of the gear arrangement 14 is above a certain level any bias provided by the outlet 38 of the container 40 may not be sufficient to effectively return the actuator 15 to its first position alone. Accordingly, the motor 12 is configured to run in reverse as discussed above. However, the motor 12 and any bias provided by the outlet 38 of the container 40 may work in combination to return the actuator 15 to its first position thereby reducing the overall energy consumption of the motor 12 when compared with using only the motor 12 to reset the position of the actuator 15.

FIG. 5 illustrates an embodiment of a dispensing device 50 in accordance with the invention, which includes the control mechanism 10 described above.

The dispensing device 50 includes an outer housing 52 which houses the control mechanism 10. The control mechanism 10 may be secured within the housing 52 using any suitable fixing means, as will be appreciated.

Specifically, the housing 52 defines a compartment 56 for housing the control mechanism 10. The compartment 56 is primarily inaccessible to prevent interference with the control mechanism 10. However, the compartment 56 includes a moveable cover 58 for providing access to a portion of the compartment 56. The cover 58 allows access to an internal portion of the housing 52 containing the power terminals 30*a*, 30*b* and the switch mechanism 36. Accordingly, cover 58 may allow access to this internal portion of the housing 52 to interact with a switch mechanism 36 of the control mechanism 10 (e.g. to change an operational setting of the control mechanism 10), or to replace the battery 32, as required. In the illustrated embodiment, the cover 58 coupled to the housing 52 via pivoted tabs and an interference-fit peg 60.

The housing 52 additionally defines a further compartment 53 in which a container 40 may be received, in use. The compartment 53 is configured such that the container 40 may be located within the compartment 53 with the outlet 38 of the container 40 positioned proximal to the actuator 15 of the control mechanism. In addition, the housing 52 includes an aperture 54 through which fluid from within the container 40 may be dispensed—specifically via an orifice 44 in the outlet 38. The compartment 53 may be accessible such that the container 40 may be replaced, as necessary. For example, the compartment 53 can include a moveable (e.g. hinged/screw thread/bayonet) or removable cover (not shown) for providing access to the compartment 53 for replacing the container.

FIG. 6 illustrates the dispensing device 50 in use. In this embodiment, housing 52 is configured such that the control mechanism 10 is provided above the container 40 such that the actuator 15 of the control mechanism 10 may act downwardly on the outlet 38 of the container to dispense fluid therefrom. The control mechanism 10 may contribute to a significant portion of the overall weight of the device 50, particularly where the amount of fluid in the container 40 is low. Accordingly, the improvements in packaging and weight realised by the control mechanism 10 of the present invention may reduce or eliminate any instability caused by having a control mechanism 10 positioned relatively high within the housing 52 of the device 50.

The one or more embodiments are described above by way of example only. Many variations are possible without departing from the scope of protection afforded by the appended claims.

The invention claimed is:

1. A control mechanism for controlling dispensing of fluid from a container, the control mechanism comprising:
a motor;
a gear arrangement operably connected to the motor; and
an actuator operably connected to the gear arrangement and configured to actuate an outlet of the container to dispense fluid therefrom under operation of the meter motor, wherein the outlet comprises a push button valve having a bias;

wherein the gear ratio of the gear arrangement is at least 190:1, and
the motor comprises a stall torque of not more than 70 gram centimeters (gcm).

2. The control mechanism of claim 1, wherein the gear ratio of the gear arrangement is at least 240:1.

3. The control mechanism of claim 1, wherein the gear ratio of the gear arrangement is 279:1.

4. The control mechanism of claim 3, wherein the motor comprises a stall torque of 35 gram centimeters (gcm).

5. The control mechanism of claim 1, wherein one or more components of the control mechanism are provided integral with, mounted to or printed on a circuit board.

6. The control mechanism of claim 4, wherein the one or more components include motor terminals for electrically coupling the motor to further components of the control mechanism, power terminals for electrically coupling a source of power, one or more processors; and/or a switch arrangement for switching an operating mode of the control mechanism.

7. The control mechanism of claim 1, which comprises a driver gear operably connected to the motor; and a driven gear configured to rotate upon rotation of the driver gear.

8. The control mechanism of claim 1, which comprises one or more intermediary gears operably coupled to the driver gear, driven gear and/or one or more further intermediary gears.

9. The control mechanism of claim 7, wherein the one or more intermediary gears comprise a compound gear having a primary set of teeth and a secondary set of teeth, with the primary set of teeth operably coupled to a preceding gear in the gear arrangement and the secondary set of teeth operably coupled to a subsequent gear in the gear arrangement.

10. The control mechanism of claim 1, wherein the actuator is integrally formed with a gear of the gear arrangement and is configured to actuate an outlet of the container to dispense fluid therefrom under operation of the motor.

11. The control mechanism of claim 1, wherein the actuator is moveable between a first position and a second position under the operation of the motor and, in use, is configured to actuate the outlet of the container in moving from its first position to its second position.

12. The control mechanism of claim 1, wherein the actuator is biased to the first position by means of a bias provided by the outlet of the container, in use, or by means of a biasing member of the control mechanism.

13. The control mechanism of claim 1, wherein the motor is configured to run in reverse to move the actuator back to its first position following actuation of the outlet of the container.

\* \* \* \* \*